(12) United States Patent
Potier (10) Patent No.: US 9,575,064 B2
(45) Date of Patent: Feb. 21, 2017

(54) METHODS RELATING TO TESTING FOR LYSOSOMAL STORAGE DISORDERS

(71) Applicant: PerkinElmer Health Sciences, Inc., Waltham, MA (US)

(72) Inventor: Anna M. Potier, Framingham, MA (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 199 days.

(21) Appl. No.: 14/474,524

(22) Filed: Sep. 2, 2014

(65) Prior Publication Data

US 2016/0061836 A1  Mar. 3, 2016

(51) Int. Cl.
| | | |
|---|---|---|
| C12Q 1/34 | (2006.01) | |
| A61K 8/36 | (2006.01) | |
| G01N 33/573 | (2006.01) | |
| A61K 38/00 | (2006.01) | |

(52) U.S. Cl.
CPC .............. *G01N 33/573* (2013.01); *C12Q 1/34* (2013.01); *G01N 2333/916* (2013.01); *G01N 2333/924* (2013.01); *G01N 2333/928* (2013.01); *G01N 2333/94* (2013.01); *G01N 2800/04* (2013.01)

(58) Field of Classification Search
None
See application file for complete search history.

(56) References Cited

U.S. PATENT DOCUMENTS

| | | |
|---|---|---|
| 7,563,591 B2 | 7/2009 | Chamoles |
| 8,173,784 B2 | 5/2012 | Cerda et al. |
| 8,476,414 B2 | 7/2013 | Cerda |
| 8,747,550 B1 * | 6/2014 | Walloch .................. C04B 28/02 106/691 |
| 2008/0248512 A1 | 10/2008 | Zhang et al. |
| 2011/0190218 A1 * | 8/2011 | Cato .................. C07K 14/4747 514/19.4 |
| 2012/0190043 A1 | 7/2012 | Cerda et al. |
| 2014/0027798 A1 | 1/2014 | Sato et al. |

FOREIGN PATENT DOCUMENTS

WO    2007/106816 A2    9/2007

OTHER PUBLICATIONS

Li et al. (2004) Direct Multiplex Assay of Lysosomal Enzymes in Dried Blood Spots for Newborn Screening, Clin. Chem., vol. 50, pp. 1785-1796.*
De Jesus et al. (2009) Development and Evaluation of Quality Control Dried Blood Spot Materials in Newborn Screening for Lysosomal Storage Disorders, Clin. Chem., vol. 55, No. 1, pp. 158-164.*
Krzystanek et al. (2010) Fluorometric assay of oleate-activated phospholipase D isoenzyme in membranes of rat nervous tissue and human platelets, Acta ABP Bioch. Polinica, vol. 57, No. 3, pp. 369-372.*
Touny et al. (1990) Regulation of Platelet Protein Kinase C by Oleic Acid . Kinetic analysis of allosteric regulation and effects on autophosphorylation, phorbol ester binding, and susceptibility to inhibition, J. Biol. Chem., vol. 265, pp. 16437-16443.*
Pittman DW (2010) Chapter 4 "Role of the Gustatory System in Fatty Acid Detection in Rats", in Book "Fat detection", Ed. by Montmayeur et al., pp. 1-4.*
Moomaw, E.W. et al., "Membrane Inlet Mass Spectrometry Reveals that Ceriporiopsis Subvermispora Bicupin Oxalate Oxidase is Inhibited by Nitric Oxide", Biochemical and Biophysical Research Communications (2014) 450: 750-754.
International Search Report and Written Opinion cited in co-pending application Serial No. PCT/US2015/048097, filed Sep. 2, 2015, 11 pages.
Gelb, Michael H. et al., "Direct multiplex assay of enzymes in dried blood spots by tandem mass spectrometry for the newborn screening of lysosomal storage disorders," J Inherit Metab Dis (2006) 29:397-404.
Li, Yijun et al., "Direct Multiplex Assay of Lysosomal Enzymes in Dried Blood Spots for Newborn Screening," Clinical Chemistry 50:10 1785,1796 (2004).
Zhang, X.K. et al., "Multiplex Eyzyme Assay Screening of Dried Blood Spots for Lysosomal Storage Disorders by Using Tandem Mass Spectrometry," Clinical Chemistry 54:10 1725-1728 (2008).
Kanicky, J.R., "Effect of Degree, Type, and Position of Unsaturation on the pKa of Long-Chain Fatty Acids," Journal of Colloid and Interface Science, 256, 201-207 (2002.
Chamoles, N.A., "Hurler-like Phenotype: Enzymatic Dianosis in Dried Blood Spots on Filter Paper," Clinical Chemistry 47:12 2098-2102 (2001).
Chamoles, N.A., et al. Diagnosis of a-L-Iduronidase Deficiency in Dried Bloood Spots on Filter Paper: The Possibility of Newborn Diagnosis, Clinical Chemistry, vol. 47, No. 4, 780-781, Apr. 2001.

* cited by examiner

*Primary Examiner* — Anand Desai
*Assistant Examiner* — Samuel Liu
(74) *Attorney, Agent, or Firm* — Dinsmore & Shohl LLP; Weston Gould (57) ABSTRACT

Processes are provided that include additive compounds suitable for detecting the activity of an enzyme such as a lysosomal storage enzyme where the additive is a salt of oleic acid. Inclusion of a salt of oleic acid unexpectedly improves enzyme activity and reproducibility.

19 Claims, 5 Drawing Sheets

FIG. 5

METHODS RELATING TO TESTING FOR LYSOSOMAL STORAGE DISORDERS

FIELD OF THE INVENTION

The present description relates to analytical reagents for detecting enzymatic activity. Detection of lysosomal enzyme activity is provided that may be used for screening assays for the detection of one or more lysosomal storage disorders.

BACKGROUND OF THE INVENTION

Lysosomal storage disorders are a group of inherited disorders characterized by deficiencies in specific enzymes in the body, which results in the body's inability to break down metabolic substances. As an example, Fabry disease is a lysosomal storage disorder seen in one out of every 40,000 people. It is caused by a deficiency in the enzyme alpha-galactosidase which results in the body's inability to break down specific fatty substances called globotriaosylceramides. A second example is Gaucher disease, a lysosomal storage disorder caused by an inability to break down fatty substances or lipids called glucosylceramides (also called glucocerebrosides). Individuals with Gaucher disease do not make glucocerebrosidase, an enzyme needed to break down these fatty substances. These fatty substances then accumulate in cells of the liver, spleen, and bone marrow. A third example is Pompe disease, a lysosomal storage disorder caused by a deficiency in the enzyme acid alpha-glucosidase, which is needed to break down certain sugars called glycogen. When the enzyme acid alpha-glucosidase is missing, glycogen accumulates in various tissues and organs in the body.

Lysosomal storage disorders are, for the most part, childhood disorders although some manifest in adulthood. In most of them, patients are normal at birth and have progressive neurological deterioration beginning at some later time. The clinical phenotype depends on the type and severity of the biochemical defect. Some of these lysosomal disorders, such as Pompe disease and Krabbe disease, manifest primarily in infancy. There have been ongoing efforts in developing methods to detect such disorders before the onset of clinical symptoms so that therapeutic interventions can be initiated.

Most of the screening tests for a lysosomal storage disorder (LSD) offered today are based on the mass spectrometry method and materials described by Zhang et al. (*Methods Mol Biol.* 2010; 603: 339-350). This method, for six LSDs (Pompe, Krabbe, Niemann-Pick A&B, Fabry, Gaucher, and MPS-1), conducts the six enzyme activity assays in six separate vessels using six separate conditions. Multiplex assays for the same disorders have been described (Scott et al, *J Pediatr.* 2013 August; 163(2):498-503; Spazil et al, *Clin Chem.* 2013 March; 59(3):502-11). Multiplex methods require less laboratory labor and reagents but it is generally more difficult to produce assay results of similar quality to non-multiplex methods where the assay conditions need to represent a compromise that supports adequate activity of the target enzymes while suppressing any confounding processes. Various enzyme activity enhancers and suppressors are added to multiplex buffers to support an optimized condition that allows each of the targeted enzymes to act measurably on its specific artificial substrate.

Oleic acid has been identified as an enhancer for the galactocerebrosidase (GALC) enzyme, for which low activity is associated with Krabbe disease (Zhang et al, ibid; Zhang et al *Clin Chem.* 2008; 54(10): 1725-1728; Li et al, *Clin Chem.* 2004; 50(10): 1785-1796). This acid has been added to buffers for Krabbe disease screening. However, oleic acid is very difficult to dissolve in aqueous buffers and the resulting varying concentration in assay buffer has led to assay results with poor reproducibility. For this reason, most published protocols for Krabbe disease screening omit oleic acid as the reproducibility problems outweigh any potential performance advantages from enhanced enzyme activities.

Thus, there is a continuing need for improving the methods and compositions for detecting lysosomal disorders.

SUMMARY OF THE INVENTION

The following summary is provided to facilitate an understanding of some of the innovative features unique to the provided processes and is not intended to be a full description. A full appreciation of the various aspects of the processes can be gained by taking the entire specification, claims, drawings, and abstract as a whole.

Improved compositions and processes for detecting enzymatic reactions using detection systems such as mass spectrometry are provided. These compositions and processes provide for improved reactivity with a target enzyme thereby improving assay efficiency, reproducibility, and accuracy.

Provided are chemical compounds for inclusion in an assay useful for assessing the level of lysosomal enzyme activity in a sample. Testing of lysosomal enzyme activity is useful, for example, when screening for metabolic disorders in newborns as well as when assessing an individual having a medical condition affecting enzyme activity or one undergoing a medical treatment such as enzyme replacement therapy, gene therapy, or bone marrow transplantation. The use of an oleate salt or alkyl oleate as described herein improves target enzyme activity toward synthetic substrates.

It is one object of the description to provide one or more additives to a reaction suitable for detecting the activity of an enzyme, illustratively an enzyme the deficiency of which leads to a lysosomal storage disorder. An additive is optionally a salt of oleate, optionally sodium oleate. An additive is optionally an alkyl oleate, optionally methyl oleate. One or more additives is optionally added to one or more components of an assay for storage prior to assay processes, or is optionally added to the assay as a soluble material. As such, provided are methods for the detection of the presence, absence, or level of an enzyme, or for the detection of the presence or absence of an enzyme deficiency in a subject. An enzyme is optionally an enzyme for which a deficiency in the enzyme leads to a lysosomal storage disorder. Use of the an oleate salt or alkyl oleate in a method for the detection of the presence, absence, or level of an enzyme allows improved confidence in assay results from the improved reactivity and reproducibility achieved as a result of the additive. A method for detecting enzymatic activity includes contacting a sample containing a target enzyme with a substrates and an additive under conditions wherein the target enzyme is capable of acting on the substrate to produce an enzymatic product; and detecting the enzymatic product. Optionally, the said target enzyme is acid β-glucocerebrosidase, acid galactocerebroside β-galactosidase or acid-β-glucocerebrosidase.

The step of detecting is optionally by mass spectrometry, optionally by multiple reaction monitoring such as in MS/MS. The step of detecting is optionally by immunoassay, substrate cleavage fluorescence assay, HPLC, mass spectrometry, or other suitable method for detecting molecules with a molecular weight less than 1000 Daltons.

DETAILED DESCRIPTION OF THE INVENTION

The following description of particular embodiment(s) is merely exemplary in nature and is in no way intended to limit the scope of the processes, its application, or uses, which may, of course, vary. The compositions or processes are described with relation to the non-limiting definitions and terminology included herein. These definitions and terminology are not designed to function as a limitation on the scope or practice of the assay or assay system but are presented for illustrative and descriptive purposes only. While the processes or compositions are described as an order of individual steps or using specific materials, it is appreciated that steps or materials may be interchangeable such that the description may include multiple parts or steps arranged in many ways as is readily appreciated by one of skill in the art.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

The compositions provided have utility as analytical reagents for detecting hydrolase enzyme activity, such as lysosomal enzyme activities associated with lysosomal storage disorders. Through the application of a salt of oleic acid (oleate salt) or an alkyl oleate, detections systems are unexpectedly found to be more robust and reproducible such that detecting enzyme activities associated with lysosomal storage disorders is more practical and less cumbersome.

Processes are provided for the detection of one or more hydrolase enzymes. Illustrative examples of hydrolases include: acid α-galactosidase A (GLA), acid β-glucocerebrosidase (ABG), galactocerebrosidase (GALC), acid α-glucosidase (GAA), acid sphingomylenase (ASM), and α-L-iduronidase (IDUA). The action of these enzymes over a substrate is used to measure the corresponding enzyme activities in a sample and thus the processes may be used to detect the following lysosomal storage disorders: Fabry (GLA); Gaucher (ABG); Krabbe (GALC); Pompe (GAA); Niemann-Pick (A or B) (ASM); and mucopolysaccharidosis (IDUA).

The activity of a particular enzyme can be assessed by its capability or rate of acting on a cognate substrate to produce enzymatic products. By determining the amount of an enzymatic product in a sample, the activity of the target enzyme can be determined. For applications in which a quantitative assessment of enzymatic product is desired, a known amount of an internal standard can be included in the sample.

A process of detecting the activity of an enzyme includes: contacting a sample containing a target enzyme with a substrate and one or more oleate salts, said step of contacting under conditions wherein the target enzyme is capable of acting on the substrate to produce an enzymatic product; and detecting the enzymatic product. The inventors surprisingly discovered that unlike oleaic acid, the use of a salt of oleaic acid produces improved enzyme activity, detection of lower enzyme amounts, and greater reproducibility. This is particularly surprising given that oleaic acid has a pKa of 9.85 (Kanicky J R and Shah D O, *J Colloid interface Sci.* 2002 Dec. 1; 256(1):201-7. As such, a process optionally excludes the addition of oleaic acid at any point in the preparation for or performance of the assay.

A process includes combining one or more oleate salts or one or more alkyl oleates with a target enzyme. An oleate salt optionally includes a monovalent or polyvalent salt. In some embodiments, an oleate salt includes a divalent salt. Illustrative examples of an oleate salt include but are not limited to sodium oleate, potassium oleate, lithium oleate, magnesium oleate, calcium oleate, zinc oleate, or any combination of two or more of said oleate salts. Optionally, 1, 2, 3, 4, 5, 6 or more oleate salts are included. Optionally, a process includes combining one or more alkyl oleates with a target enzyme. An alkyl oleate is optionally a $C_1$-$C_4$ oleate, where the $C_3$ or $C_4$ is optionally linear or branched. The remainder of the description is directed to use of the term oleate salt, but it is appreciated that in each instance an alkyl oleate may be substituted for or added to the oleate salt.

An oleate salt is optionally combined with a substrate, an internal standard, or both prior to contacting an enzyme. In some embodiments, an oleate salt is contacted with a substrate, an internal standard, or both, to form a substrate component, and the substrate component is then subjected to a drying step. Drying is achieved by any one or more drying methods recognized in the art. Drying is optionally achieved by evaporation under vacuum, by evaporating under nitrogen or other inert gas, or by lyophilization. Methods of drying samples are well known in the art.

The oleate salt and substrate, optionally in the form of a substrate component, are optionally combined with a target enzyme. Illustrative examples of a target enzyme include, but are not limited to, α-galactosidase A, acid β-glucocerebrosidase, galactocerebrosidase, acid α-glucosidase, acid sphingomylenase, α-L-iduronidase, or combinations of two or more of the target enzymes. Optionally, 1, 2, 3, 4, 5, 6, or more target enzymes are assayed simultaneously or sequentially. In some embodiments, a multiplex assay is used where two or more enzymes are assayed simultaneously. Optionally, 2, 3, 4, 5, 6, or more enzymes are assayed simultaneously. Optionally, 1, 2, 3, 4, 5, 6, or more enzymes are assayed individually or sequentially.

The activities of certain lysosomal enzymes in the blood of an individual can be used to test whether that individual has a lysosomal storage disorder. Therefore, substrates specific for one or more target enzymes are optionally used as a substrate in a process. Such substrates are optionally suitable for detecting a medical condition, in particular, lysosomal storage disorders such as Gaucher disease, Krabbe disease, Niemann-Pick disease, Pompe disease, Fabry disease, or mucopolysaccharidosis.

While the processes provided are not so limited, illustrative substrates and internal standards suitable for inclusion in a process are described in: U.S. patent application Ser. No. 14/215,885; U.S. Pat. No. 8,476,414; U.S. Pat. No. 8,173,784; U.S. Publication No: US 2012/0190043; WIPO Publication No: WO 2007/106816; Gelb et al., *J Inherit. Metab. Dis.*, (2006) 29:397-404; Li, et al., *Clinical Chemistry*, 50; 10:1785-1796 (2004); among others.

A process optionally includes use of an internal standard that is optionally combined with a substrate and an oleate salt prior to contacting one or more enzymes. An internal standard functions as an experimental control or standard useful for assessing the amount of enzymatic product in a sample or sample receptacle. For use in mass spectrometry methods, an internal standard corresponding to a particular substrate is optionally structurally identical to its enzymatic product (e.g. fatty acid portion), except that the internal standard differs in mass-to-charge (m/z) ratio. Thus, the internal standards optionally include modified forms of enzymatic products, for example, stable isotope-labeled analogs of enzymatic products in which one or more atoms are replaced by corresponding atomic isotopes so as to create a differentially detectable mass difference with the corresponding enzymatic product. When the internal standard and enzymatic product are analyzed by mass spectrometry, the resulting spectrum reveals a spatial separation of the internal standard and enzymatic product, each represented by its own peak. The known amount of internal standard is reflected by peak magnitude at its known m/z ratio. The amount of enzymatic product can be assessed by comparison of peak magnitude at its known m/z, relative to the peak magnitude of the internal standard. An example of isotopic labeling to produce an internal standard is the replacement of $^1$H with $^2$H (i.e. deuterium, D). As a result, a "heavier" internal standard molecule with the substituted $^2$H has a different m/z from the enzymatic product, as detected on a mass spectrum. In a particular embodiment, an internal standard is labeled with deuterium to cause a mass change of 3 to 9 Daltons from the corresponding cleaved product.

A substrate can be used in a variety of physical formats, for example, in solution, in dry form, as well as linked or immobilized to solid supports. A solid support can be composed of a natural or synthetic material, an organic or inorganic material, such as a polymer, resin, metal or glass, and combinations thereof. A suitable solid support can have a variety of physical formats, which can include for example: a membrane; column; a hollow, solid, semi-solid, pore or cavity-containing particle such as a bead; a gel; a fiber, including a fiber optic material; a matrix; and sample receptacle. Non-limiting examples of sample receptacles include sample wells, tubes, capillaries, vials and any other vessel, groove or indentation capable of holding a sample. A sample receptacle can be contained on a multi-sample platform, such as a microplate, slide, microfluidics device, and the like. Many suitable particles are known in the art and illustratively include Luminex®-type encoded particles, encoded fiber optic particles, magnetic particles, and glass particles. Covalent interaction of a substrate and/or enzymatic cleavage product thereof with a solid support is useful for retaining the substrate and/or product during washing procedures performed in some assay formats, thus, producing a robust and accurate signal of enzymatic activity.

The processes described herein are optionally performed in a multiplexed format such that a plurality of enzymes are assayed simultaneously. An illustrative example of a multiplex format is the inclusion of several different substrates, internal standards, samples, enzymes, or other, or combinations thereof on a single multi-well plate. Optionally, a multiplex format includes the presence of multiple enzymes, samples, substrates, internal standards, others or combinations thereof in a single well or assay container. Another illustrative multiplexed format involves using physically and/or chemically coded particles. Use of coded particles in multiplexed formats has been described, for example, in U.S. Pat. No. 6,649,414 and U.S. Pat. No. 6,939,720. Because the codes allow particles to be distinguished from each other, a plurality of distinct particles can be present in a single reaction mixture, allowing a plurality of different samples or different enzymes to be assayed simultaneously. Codes on particles can correspond, for example, to sample origins, particular enzymes to be assayed, particular substrates present, and the like, depending on the experimental goal of the user.

A sample useful in the processes provided contains or is suspected of containing one or more target enzymes. Target enzymes can be contained in samples obtained from an individual, as well as from laboratory or synthetic materials, such as cell lines, and synthetic protein sources. Exemplary sample sources illustratively include: tissue homogenates; cell culture lysates; and biological fluids including urine, blood in liquid or dry form, tears, saliva, and cerebrospinal fluid. A sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample, and the like. In a specific embodiment, the sample is blood, which can be, for example, whole blood or a blood fraction thereof (e.g. plasma or serum), or reconstituted from a dried blood sample.

Methods for obtaining samples that preserve the activity or integrity of molecules in the sample are well known to those skilled in the art. Such methods include the use of appropriate buffers and/or inhibitors, including nuclease, protease and phosphatase inhibitors, which preserve or minimize changes in the molecules in the sample. Such inhibitors include, for example, chelators such as ethylenediamine tetraacetic acid (EDTA), ethylene glycol bis(P-aminoethyl ether)N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)). A sample also can be processed to eliminate or minimize the presence of interfering substances.

Samples in the form of a dried blood spot are commonly used when screening blood from newborns and child patients. To prepare these samples, blood is collected and retained on filter paper. For analysis, the dried blood is optionally eluted from a portion of the filter paper into an aqueous solution, which generally contains a buffer such as phosphate buffered saline, HEPES, Tris, succinate, or other buffer, and optionally one or more protease inhibitors. Specific examples of protease inhibitor conditions include for example, one or more of the following: AEBSF hydrochloride in a final concentration of 50 to 400 μg/ml, EDTA disodium dehydrate in a final concentration of 0.2 to 25 mg/ml, leupeptin hemisulfate in a final concentration of 0.5 to 1 μg/ml, and pepstatin A in a final concentration of 0.5 to 1 μg/ml. Protease inhibitor cocktails known commonly used in the art may be used. The use of a universal assay solution to extract a single dried blood sample, or other type of sample, for subsequent distribution into multiple assay reactions can be used for automatic and high throughput screening. A single extraction of a dry sample avoids the need to obtain several sample punches from the same sample, or to collect aliquots of other sample sources and accordingly reduces variation caused by inhomogeneous distribution of blood on the filter paper and errors in sample transfer. When using dry samples, extraction efficiency may vary with the different enzymes being analyzed. In these and other types of samples, the target enzymes may have different levels of activities when contained in different assay solutions. A composition of a universal assay solution is optionally chosen such that each enzyme to be tested is active.

In some embodiments, the dried blood spot or a punch derived from it is placed directly into an assay buffer including one or more substrates and an oleate salt, and optionally internal standards, and allowed to incubate for a time sufficient to allow enzymes present in the sample to convert the substrate(s) to product(s) prior to detection by one or more detection methods.

The substrates and products provided can be used in a variety of assay formats. The substrate can be detected in an assay when it is desired to observe substrate consumption during an enzymatic assay, while the product can be detected in the assay when it is desired to observe its formation during an enzymatic assay. Both substrate and product can be detected when it is desired to observe the enzymatic reaction from both perspectives, for example, to confirm that the amount of product produced correlates with the amount of substrate consumed.

For example, the amount of substrate or product are optionally detected using established tandem mass spectrometry procedures. An exemplary enzyme assay employing mass spectrometry is optionally performed as follows. A sample is incubated with a substrate and oleate salt in an aqueous assay buffer for a time period that allows formation of an enzymatic product. During the incubation period, the substrate is cleaved by a target enzyme present in a blood sample to form a respective product. The reaction is then quenched by adding a reagent that precipitates protein components. Exemplary reagents include alcohol, acetonitrile and dilute trifluoro acetic acid. A portion of the incubation mixture is then transferred to a new assay vessel. Optionally, a dilution reagent such as methanol, acetonitrile, water-methanol mixtures or water-acetonitrile can be added to dilute the transferred portion. The sample so diluted reduces the amount of endogenous competing material so as to relatively increase the sensitivity of the tandem mass spectrometry analysis. Other types of reagents are selected by those skilled in the art to be compatible with analyses by mass spectrometry of many varieties, or other detection systems.

In some embodiments, the diluted sample is directly injected into the tandem mass spectrometer either manually or automatically with the aid of autosamplers and liquid handlers. If desired, the sample can be derivatized prior to analysis. Reagents are selected to be non-hostile to the MS/MS system. For example, suitable solvents lack detergents and corrosive agents, such as chloroform. Pure ethanol and pure methanol are often used simply because they easily vaporized upon mechanical drying processes.

The tandem mass spectrometer can be set to simultaneously detect the added substrate, the corresponding resulting enzymatic product and the corresponding internal standards. Such detection is accomplished by means of parent ion scans, precursor ion scans or multiple reaction monitoring scans.

In some aspects, the amount of substrate consumed or product formed during an enzymatic assay is detected based on a fluorescence signal from the substrate and/or product. Such fluorescence based assays for lysosomal storage disorders have been reported in the literature (see, for example, N. A. Chamoles, et al. *Clinical Chemistry*, 2001; 47(12): 2098-2102, and N. A. Chamoles, et al. *Clinical Chemistry*, 2001; 47(4):780-781). A general overview of this approach is that a fluorescently labeled substrate (for example, a substrate labeled with 4-methyllumbelliferone) is introduced to a test sample containing the enzyme and incubated for a sufficient time, typically at room temperature or 37° C. A stop solution is added to stop the assay and adjust the pH to 10. The samples are then read using a fluorometer. The fluorescence intensities recorded with the test samples are converted to the amount of product formed by using a 4-MU standard curve.

The amount of substrate consumed or product formed during an enzymatic assay also can be detected using antibodies and other target-specific binding molecules. For immunoassays, an antibody can be used to detect the substrate, product or both. Antibodies useful in such methods can be specific, such that they recognize individual substrates, or non-specific, such that they recognize many or all substrates. A substrate or product optionally includes a label such as biotin or avidin to allow specific detection.

The antibody is illustratively produced in animals including mouse, rat, rabbit, horse, donkey, or other suitable animal used for the production of antibodies. In some applications, it is useful to label an antibody with a detectable tag, such as a fluorescent tag. When using an unlabeled antibody, detection can be performed by using a secondary antibody that is specific for the species IgG of the primary antibody is labeled illustratively with a fluorescent marker such as rhodamine. It is appreciated in the art that other antibody detection systems are similarly operable such as horseradish peroxidase labeled antibodies, or alkaline phosphatase labeled antibodies.

When testing multiple enzymes in a single sample by providing multiple enzyme-specific substrates, antibodies that recognize and distinguish between the substrates, or products thereof, and be used. Complexes of antibodies bound to enzyme-specific substrates, or products thereof, can be distinguished from each other using many methods. In one scenario, samples containing target enzymes are contacted with substrates linked to particles in an assay solution. In this example, each particle is linked to a particular substrate, and there are multiple particles representing each substrate. Antibodies that recognize specific products are then contacted with the assay solution. The antibodies will bind to the products, if produced during the enzymatic assay, to produce particles having bound antibodies. To distinguish different products contained on the particles, antibodies having different product specificities can have different detectable moieties, such as different fluorescent tags. As an alternative to detecting enzymatic products, antibodies that recognize substrate can be used to detect substrate remaining on the beads after incubation with enzymes. In this situation, either product would remain attached to the bead, if an enzymatic reaction occurred. In either case the selected substrate specific antibody would not significantly cross-react with product attached to the bead.

In another scenario, samples containing target enzymes are contacted with substrates linked to encoded particles in an assay solution. The encoded particles have a feature, such as a bar code or optical profile, which allows them to be distinguished from each other. For example, encoded particles can have different bar codes corresponding to different target enzyme substrates. In the assay, the target enzymes act on the substrates to produce products. One product would remain bound to the particle, while the other product (cleaved portion) would be released into solution, or visa versa. Antibodies that recognize specific products are then contacted with the assay solution. Because the encoding of the particle indicates which substrate is attached to the particle, antibodies need not be specific for particular products, and thus one type of antibody can be used to detect products derived from multiple different substrates. Such non-specific antibodies will bind to the products, if produced during the enzymatic assay, to produce particles having bound antibodies. Particles having bound antibodies are then distinguished from those without antibodies, for example, by detecting a tag on the antibodies or physical behavior of the particles. The different products contained on the antibody-bound particles can be determined based on the encoding of each particle.

As another example of an immunoassay format, antibodies directed to particular substrates are generated. Following quenching of an enzymatic reaction, the reaction solution is transferred to a high-binding microtiter plate whereby a portion of a product will bind to a surface. The enzyme and assay solution components are removed by washing. The specific primarily antibody is then incubated in each assay well followed by subsequent washing to remove unbound antibody. A secondary antibody is optionally used for detection and quantitation. The more product formed per unit time of initial reaction the greater the activity of the measured enzyme.

An antibody is illustratively unlabeled and produced in animals including mouse, rat, rabbit, horse, donkey, or other suitable animal used for the production of antibodies. A secondary antibody that is specific for the species IgG of the primary antibody is labeled illustratively with a fluorescent marker such as rhodamine and subsequently used for detection of remaining substrate. It is appreciated in the art that other antibody detection systems are similarly operable such as horseradish peroxidase labeled antibodies, or alkaline phosphatase labeled antibodies.

In some embodiments, an assay for target enzymes is performed by first obtaining a sample illustratively including serum, plasma, whole blood, urea, saliva, other biological fluids or tissue lysates, recombinant or native purified enzyme in solution, or chemically or functionally modified enzyme in biological fluid or liquid medium. A portion of the filter paper sample is then excised and deposited in a non-binding assay tube or micro titer plate well to which an assay solution is added. The assay solution includes one or more aqueous buffers, a substrate, a standard, an oleate salt, and optionally one or more protease inhibitors. The sample mixture is then incubated for a determined period of time in the range of 30 minutes to 20 hours at a particular temperature ranging from 30° C. to 41° C. Once incubation is complete, the enzymatic reaction is terminated by addition of a stopping solution. A stopping solution is illustratively 0.4 M glycine/NaOH pH 10.4 added at 6× reaction volume. Leonard R, et al., *J. Biol. Chem.*, 2006; 281:4867-75; Boot, R G, et al., *J. Biol. Chem.*, 2006; 282:1305-12. The amount of product formation is determined by transferring a known volume of sample to a high-binding assay tube or microtiter plate and incubated for 5 minutes to 2 hours. The unbound material is removed by washing. Detection of the intact substrates or products is illustratively performed using a coupled peroxidase enzyme approach.

In a further scenario using sugar containing substrates, the level of released glucose or galactose product is measured in real time by a coupled enzyme approach. A non-limiting example involves the release of glucose from a substrate specific for β-glucocerebrosidase in diagnosis of Gaucher disease. In this assay method glucose is reacted with glucose oxidase producing glucolactone and releasing hydrogen peroxide. The released hydrogen peroxide is detected by reaction with peroxidase to produce a fluorescent molecule that is measured on a standard fluorometer. Examples of suitable peroxidases are horseradish peroxidase or any other peroxidase known in the art. The hydrogen peroxide released by glucose oxidase interacts with a detector substrate molecule. The peroxidase catalyzes conversion of this substrate to a fluorescent product. A detector molecule suitable for use with the substrates includes Amplex Red that is oxidized in to produce the fluorescent product resorufin. Amplex Red and kits for detecting free glucose are available from Invitrogen Corp. The increase in red fluorescent product is detected on a fluorometer set with an excitation wavelength at 571 and an emission wavelength at 585 with the band pass set at 5 nm. The greater amount of glycosidase activity the more rapidly the red fluorescent product is produced.

In some embodiments multiple substrates for different lysosomal enzymes are generated with unique structure(s). This prevents product inhibition of one enzyme that is particularly important should the catalytic activity of one enzyme toward one substrate be much greater than the catalytic activity of the other enzyme for its corresponding substrate. This is additionally important in conditions where a single mutant glycosidase is being screened in a panel of substrates for 6 or more lysosomal enzymes. The product formed by the other lysosomal enzymes may inhibit the function of the lower activity enzyme such that its activity is not accurately measured. Thus, the specificity of the substrate and the product for each enzyme is appreciated to be optionally distinct.

The approach described for assaying enzymes using substrate and standard compounds can be expanded to assay a plurality of enzymes simultaneously in a single reaction, obviating the need for multiple assays to assist in confirming diagnoses of medical disorders. The processes can also be used to measure several enzymes simultaneously when evaluating the rate of chemical flux through a specific biochemical pathway or for monitoring biochemical signaling pathways. Because of the high sensitivity of mass spectrometry detection employable using the compounds described herein, which can require only sub-microgram quantities of the substrate reagents per assay, the synthesis of several hundred substrate reagents on a low-gram scale becomes practical and economical.

In various embodiments two, three, four, five, six, or more lysosomal enzymes are simultaneously measured for activity by the use of substrates as provided.

As another exemplary format for use with the provided substrates, the substrates can be labeled with the same fluorophore, but possess significant mass or charge characteristics that differentiate one from the other. The amount of product produced following an enzymatic cleavage reaction is detected by reversed phase high performance liquid chromatography (HPLC). Reactions are quenched by the addition of alcohol, acetonitrile or dilute trifluoro acetic acid. A portion of the incubation mixture is transferred to a new assay vessel to which is added a neat solution such as methanol, acetonitrile, water-methanol mixtures or water-acetonitrile. The reaction products and unreacted substrate are separated on a 5 μm particle size $C_{18}$ HPLC column and detected by a fluorescent detector or set of detectors. The amount of product is calculated based on a standard curve generated using increasing amounts of the relevant product.

It is appreciated in the art that multiple substrates for multiple enzymes are optionally simultaneously detected by a chromatographic method. If substrates with sufficiently different mass or retention characteristics are used, each product is resolvable, for example, on an HPLC column and can be quantified in a single assay. Alternatively, each substrate is labeled with a different fluorophore that has different or the same excitation or emission properties. Detection may be by a family of fluorescent detectors that can simultaneously quantify individual products from each other and their corresponding labeled substrate. Other methods of detection are similarly suitable and are known in the art.

All reagents including the substrates, enzymatic products, and internal standards can be optionally purified by reverse-phase HPLC and characterized by ESI-MS, either in an online HPLC-MS assay or offline by collection of the appropriate fractions.

A process includes the contacting step in a solution including an aqueous buffer. An aqueous buffer optionally has a pH between 4 and 5. A pH is optionally from 4.5 to 5. A pH is optionally 4.5 to 4.7. A pH is optionally 4.0, 4.1, 4.2, 4.3, 4.4, 4.5, 4.6, 4.7, 4.8, 4.9, or 5.0. Any suitable buffering agent operable to act as a buffer in the desired pH range is suitable for use as an aqueous buffer. Illustrative examples of buffers include succinic acid, acetate, citrate, PIPES, or other buffer are optionally used.

In some embodiments, a substrate component is formed prior to the step of contacting the substrate with the target enzyme. A substrate component optionally includes a substrate, an oleate salt, optionally an internal standard, and an aqueous buffer. A combination of dried substrate, oleate salt, and optionally internal standard are optionally resuspended in an aqueous buffer and stored for a storage time prior to contact with a sample or target enzyme. A storage time is optionally from 1 minute to 8 weeks. The resulting substrate component has been shown to be stable for 8 weeks or more when stored at room temperature sequestered from light.

A substrate component, is optionally contacted with a sample that may or may not contain one or more target enzymes under conditions wherein the target enzyme is capable of acting on the substrate to produce an enzymatic product. The step of contacting is optionally for a reaction time. A reaction time is optionally from 1 minute to 48 hours or more. Optionally, a reaction time is from 10 to 20 hours. It is appreciated that when detecting low quantities of enzyme that longer reaction times may be used. Following a reaction time, a sample is optionally quenched to stop the reaction. A stop solution is optionally 50:50 ethyl acetate/methanol or other suitable quench solution.

Various aspects are illustrated by the following non-limiting examples. The examples are for illustrative purposes and are not a limitation on any practice of the present processes. It will be understood that variations and modifications can be made without departing from the spirit and scope of the description. Reagents illustrated herein are commercially available or readily synthesized by well-known methods from readily commercially available precursors, and a person of ordinary skill in the art readily understands where such reagents may be obtained.

EXAMPLES

Example 1

Detection Enzyme Activity in a Sample

Figure 1:
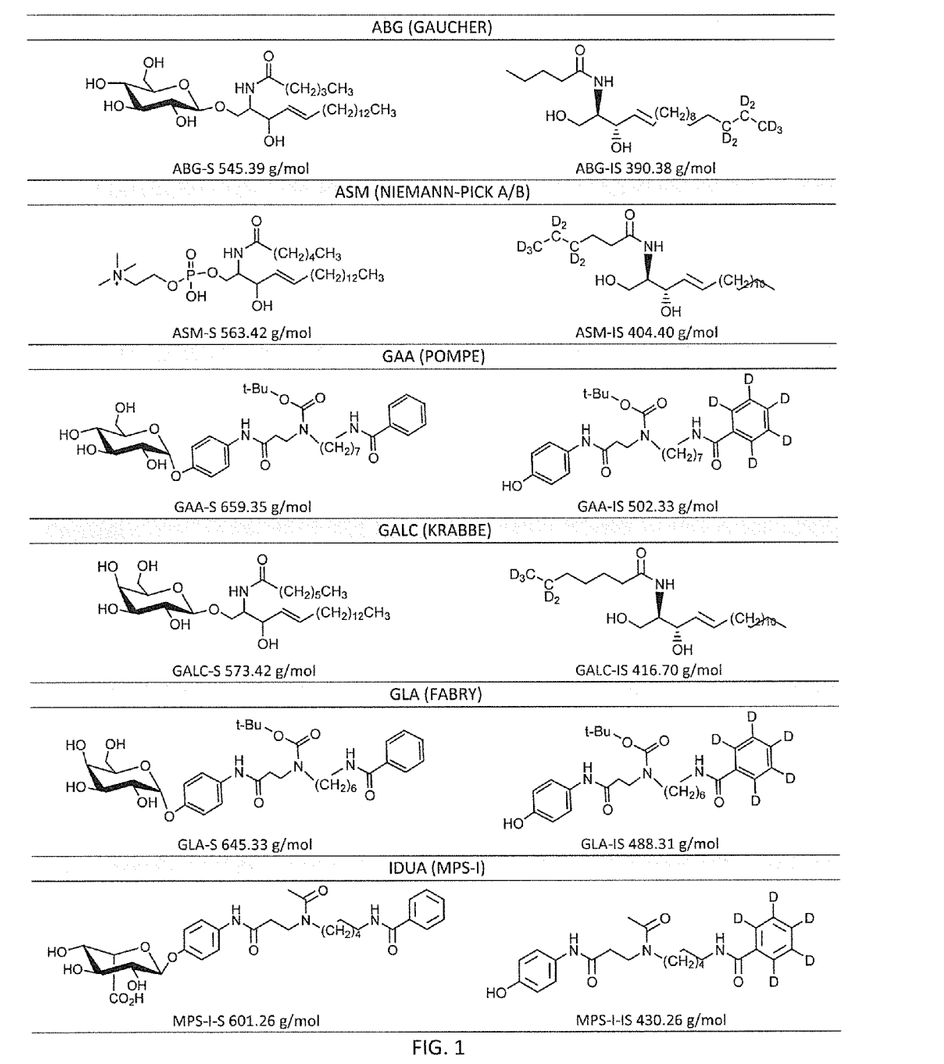
FIG. 1 illustrates exemplary substrates and internal standards used in some embodiments of a process.
Figure 2:
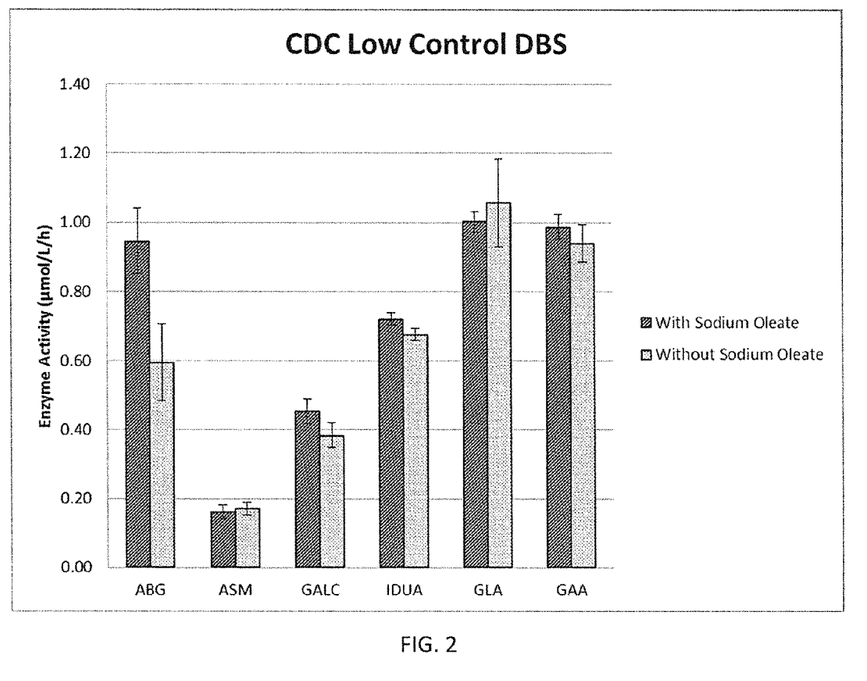
FIG. 2 illustrates enzyme activity obtained with and without the addition of sodium oleate when using low enzyme control samples.
Figure 3:
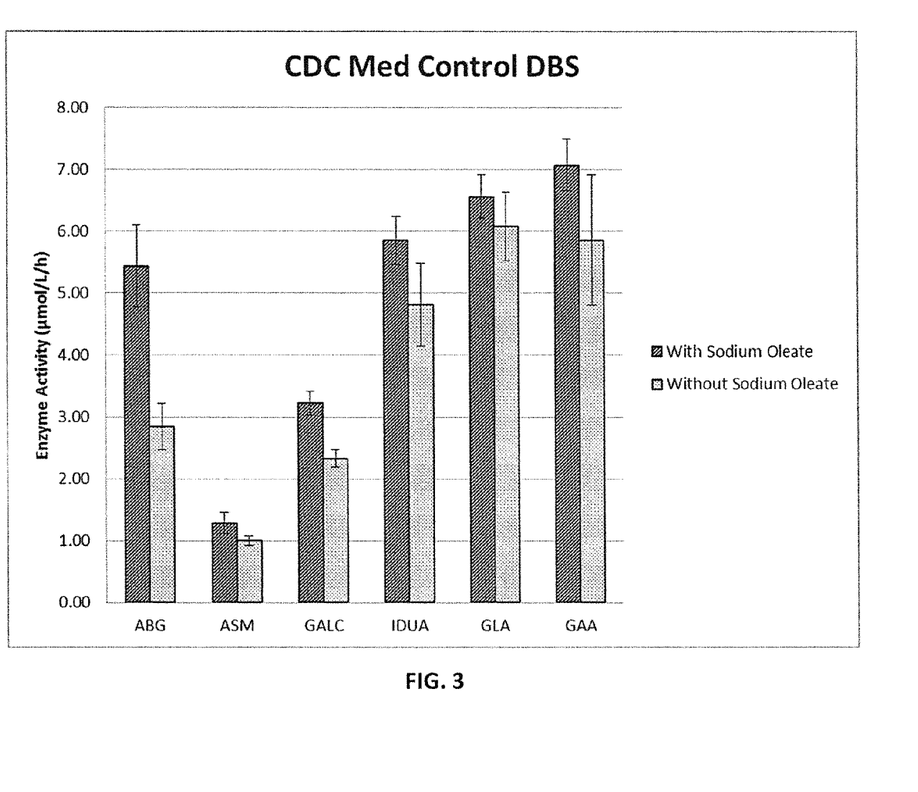
FIG. 3 illustrates enzyme activity obtained with and without the addition of sodium oleate when using medium enzyme control samples where column 1 represents acid β-glucocerebrosidase (ABG), column 2 represents acid sphingomylenase (ASM), column 3 represents GALC, column 4 represents α-L-iduronidase (IDUA), column 5 represents acid α-galactosidase A (GLA), and column 6 represents α-glucosidase (GAA)
Figure 4:
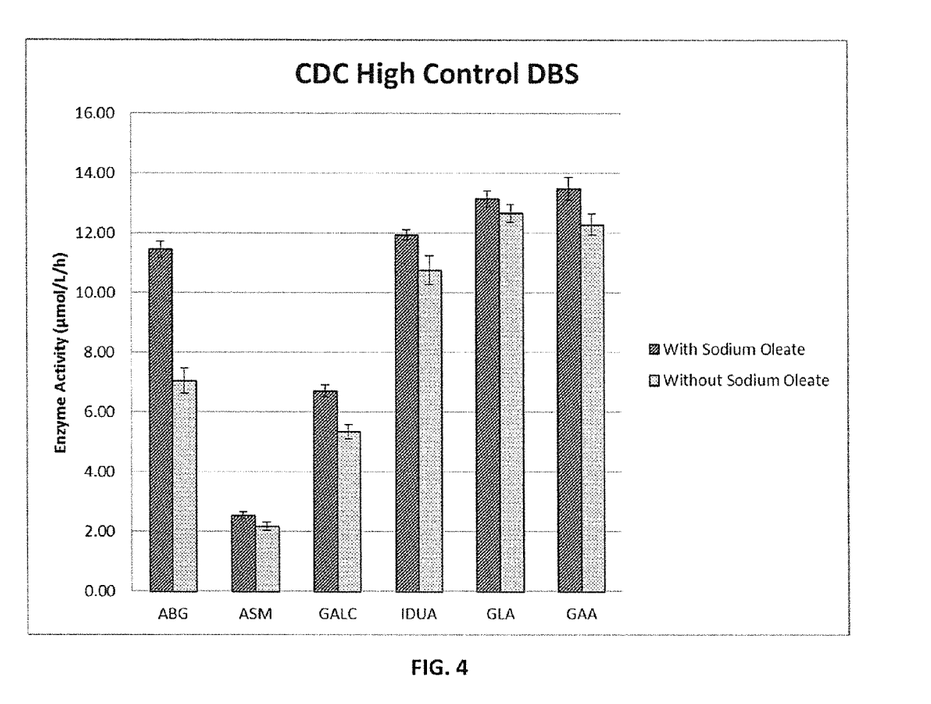
FIG. 4 illustrates enzyme activity obtained with and without the addition of sodium oleate when using high enzyme control samples where column 1 represents ABG, column 2 represents ASM, column 3 represents GALC, column 4 represents IDUA, column 5 represents GLA, and column 6 represents GAA.
Figure 5:
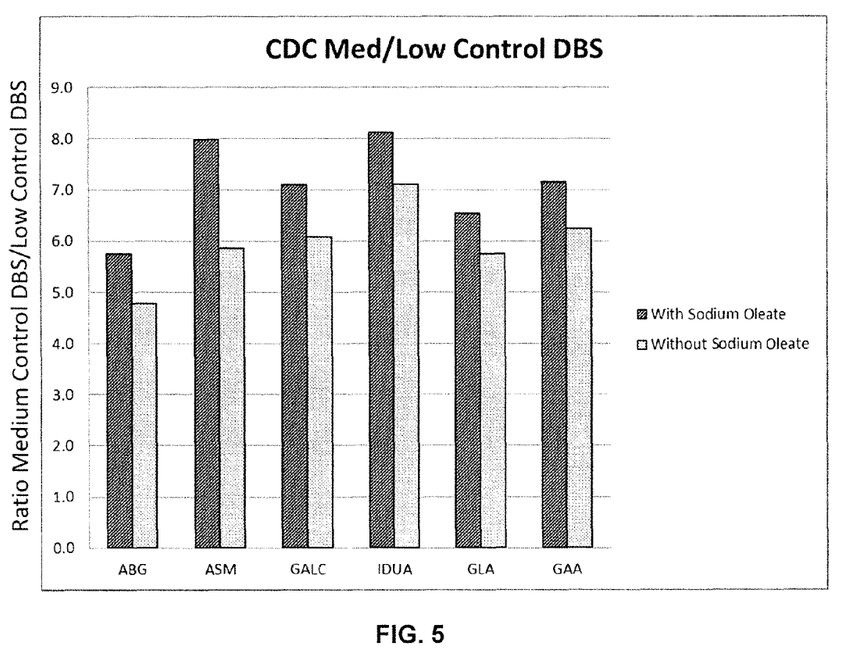
FIG. 5 illustrates the ratio obtained (Medium Control DBS/Low Control DBS) with and without the addition of sodium oleate where column 1 represents ABG, column 2 represents ASM, column 3 represents GALC, column 4 represents IDUA, column 5 represents GLA, and column 6 represents GAA.

Artificial substrates (S) and deuterated internal standards (IS) (FIG. 1) as well as the sodium oleate (CarboSynth, 97%, 143-19-1) were dissolved in LC-MS grade methanol. An aliquot of this pre-mixed stock solution was transferred to a 40 mL glass vial and dried down on a SAVANT SPEEDVAC Concentrator (Thermo Fisher) to produce a vial containing stable material in the amounts indicated in Table 1.

TABLE 1

Amount of substrate, internal standard and sodium oleate used to produce assay cocktail sufficient to analyze 960 samples.

| | Amount per 960 sample vial |
|---|---|
| | mg |
| Substrate | |
| ABG-S | 9.00 |
| ASM-S | 13.92 |
| GAA-S | 7.62 |

TABLE 1-continued

Amount of substrate, internal standard and sodium oleate used to produce assay cocktail sufficient to analyze 960 samples.
Amount per 960 sample vial

| | mg |
|---|---|
| GALC-S | 16.08 |
| GLA-S | 25.56 |
| IDUA-S | 4.96 |
| IS | |
| ABG-IS | 0.26 |
| ASM-IS | 0.20 |
| GAA-IS | 0.40 |
| GALC-IS | 0.14 |
| GLA-IS | 0.39 |
| IDUA-IS | 0.21 |
| Additive | |
| Na Oleate | 42.9 |

In a separate 60 mL bottle, 40 mL of an 85 mM succinic acid buffer, pH 4.7, was prepared which contained the additives listed in Table 2 to produce a working succinic acid buffer. Preparation of the assay cocktail was accomplished by adding 33 mL of the 85 mM working succinic acid buffer to the glass vial containing the dried components. The vial was sonicated for 10 minutes in a water bath (VWR-Model 75D) followed by gentle rocking for 20 minutes until all of the material was fully dissolved. The vial of assay cocktail was wrapped in aluminum foil and stored at room temperature away from light for up to eight weeks.

TABLE 2

Concentrations and suppliers of additives used in 85 mM succinic acid buffer, pH 4.7.

| Additive | Concentration | Supplier | Cat. Number |
|---|---|---|---|
| Acarbose | 8 μL | Carbosynth | OA00002 |
| N-acetylglucosamine | 50 mM | Carbosynth | MA04390 |
| D-saccharic acid 1,4-lactone monohydrate | 40 μM | Sigma | S0375 |
| Sodium taurocholate | 15 mg/mL | Carbosynth | FS10907 |
| Zinc chloride | 0.6 mM | Sigma | 229997 |

Blood was obtained by venipuncture from consenting adult humans and blotted on filter paper to form dried blood spots. Dried blood spots for CDC controls are made essentially as described in Jesus et al., *Clinical Chemistry*, 55:1 (2009) 158-164. Briefly, different ratios of leukocyte-reduced blood obtained by venipuncture from consenting adult humans are combined with unprocessed cord blood at various levels to adjust the amount of target enzyme. Such samples may also be obtained from unaltered adult blood or newborn blood, optionally as obtained from a heel stick. Plates for incubation with a disk of 3 mm diameter of sample dried blood spot (DBS) were loaded with the desired DBS specimen samples according to the desired plate map using a DBS puncher (PerkinElmer 1296-071) into a 0.5 mL 96-well polypropylene NUNC plate (Thermo, 267245). To each well, 30 μL of assay cocktail was added and the plates were sealed with adhesive aluminum foil (Starseal, E2796-9792). The plates were incubated for 18 hours at 37° C. with 400 RPM shaking using a TRINEST incubator shaker (PerkinElmer, 1296-0050). After 18 hours, the plates were quenched by adding a 100 μL it aliquot of a 50:50 ethyl acetate/methanol (LC-MS grade or equivalent) mixture to each well then mixing ten times with the pipette. The incubation solution was transferred from the 0.5 mL polypropylene plate to a 1 mL deep well plate (Thermo Nunc, 260252), making sure to transfer all of the solvent mixture to the deep well plate while leaving behind the DBS.

Sample cleanup was accomplished by first adding 400 μL of ethyl acetate (LC-MS grade or equivalent) to the incubation solution followed by 200 μL of water (Type 1 or better). The two layers were mixed by aspiration twenty times until an emulsion was observed. The 1 mL deep well plate was covered with the adhesive aluminum foil and centrifuged (Rotanta 460 R) for 5 minutes at 690×g. A 75 μL aliquot of the organic layer that separates on top of the aqueous layer was transferred to a 0.5 mL NUNC plate (Thermo, 267245) and dried for 5-10 minutes using compressed air. The samples were reconstituted by adding 150 μL of a flow solvent consisting of 84% acetonitrile with 0.1% formic acid (JT Baker, 53673) and 16% water with 0.1% formic acid (JT Baker, 52116). The plates were sealed with a non-adhesive aluminum foil, and then shaken at 400 rpm for 10 minutes at room temperature. The samples were analyzed by FIA-MS/MS (Waters Acquity TQD) using the transitions outlined in Table 3 as well as the global tune parameters and inlet settings indicated in Table 4.

TABLE 3

MS transitions for internal standards, IS, and products, P, detected in the assay.

| MRM | Parent (m/z) | Daughter (m/z) |
|---|---|---|
| ABG-IS | 391.4 | 271.3 |
| ABG-P | 384.3 | 264.3 |
| ASM-IS | 405.4 | 264.3 |
| ASM-P | 398.4 | 264.3 |
| GAA-IS | 503.4 | 403.3 |
| GAA-P | 498.3 | 398.3 |
| GALC-IS | 417.4 | 264.3 |
| GALC-P | 412.4 | 264.3 |
| GLA-IS | 489.3 | 389.3 |
| GLA-P | 484.3 | 384.2 |
| IDUA-IS | 431.3 | 322.2 |
| IDUA-P | 426.2 | 317.2 |

TABLE 4

Global Tune Parameters and Inlet Settings used with the Acquity TQD.

| Global Tune Parameters | | Inlet Settings | | |
|---|---|---|---|---|
| Parameter | Setting | Time (min) | Flow Rate (mL/min) | Curve |
| Capillary Voltage | 4 kV | — | 0.10 | — |
| Source Temp. | 80° C. | 0.05 | 0.10 | 11 |
| Desolvation Temp. | 170° C. | 0.10 | 0.03 | 11 |
| Desolvation Gas | 1000 L/hr | 0.65 | 0.50 | 11 |
| Cone Gas | 50 L/hr | 0.90 | 0.10 | 11 |
| | | 1.00 | 0.10 | 11 |

Peak areas for products and internal standards were calculated using the program NeoLynx. Enzymatic activity ($A_e$, μmol/L/h) was calculated using the P/IS ratio in the following equation (Eq. 1), where P/IS the ratio of intensities obtained from the MS/MS, [IS] is the concentration of IS used, $V_{IS}$ is the volume of IS used, t is incubation time, and $V_{DBS}$ is the volume of blood obtained from DBS used in the assay. For a 3 mm DBS punch, $V_{DBS}$=3 μL:

$$A_e = \frac{(P/IS) * [IS] * V_{IS}}{t * V_{DBS}} \quad \text{(Eq. 1)}$$

A comparison between two assays that only differed by the addition or lack of sodium oleate showed that the enzyme activity of the ceramides (ABG, ASM and GALC) improved when sodium oleate was present as illustrated in Table 5 and FIGS. 1-4.

TABLE 5

Enzyme activity obtained using assay cocktail with and without sodium oleate with control DBS from the Center for Disease Control, Laboratory Quality Assurance and Standardization Programs.

| Enzyme Activity (μmol/L/h) | ABG | ASM | GALC | IDUA | GLA | GAA |
|---|---|---|---|---|---|---|
| CDC Low Control DBS (with sodium oleate) | 0.95 | 0.16 | 0.45 | 0.72 | 1.00 | 0.99 |
| % CV | 10% | 12% | 8% | 3% | 3% | 4% |
| CDC Low Control DBS (without sodium oleate) | 0.60 | 0.17 | 0.38 | 0.68 | 1.06 | 0.94 |
| % CV | 19% | 11% | 9% | 3% | 12% | 6% |
| Sodium oleate gain | 159% | 95% | 118% | 107% | 95% | 105% |
| CDC Medium Control DBS (with sodium oleate) | 5.44 | 1.29 | 3.22 | 5.86 | 6.57 | 7.08 |
| % CV | 12% | 13% | 6% | 7% | 5% | 6% |
| CDC Medium Control DBS (without sodium oleate) | 2.85 | 1.00 | 2.34 | 4.82 | 6.08 | 5.87 |
| % CV | 13% | 7% | 6% | 14% | 9% | 18% |
| Sodium oleate gain | 175% | 122% | 133% | 116% | 106% | 115% |
| CDC High Control DBS (with sodium oleate) | 11.46 | 2.54 | 6.72 | 11.95 | 13.15 | 13.48 |
| % CV | 2% | 4% | 3% | 1% | 2% | 3% |
| CDC High Control DBS (without sodium oleate) | 7.05 | 2.18 | 5.35 | 10.77 | 12.68 | 12.29 |
| % CV | 6% | 6% | 4% | 4% | 2% | 3% |
| Sodium oleate gain | 162% | 117% | 126% | 111% | 104% | 110% |
| CDC Med/Low Control DBS (with sodium oleate) | 5.8 | 8.0 | 7.1 | 8.1 | 6.5 | 7.2 |
| CDC Med/Low Control DBS (without sodium oleate) | 4.8 | 5.9 | 6.1 | 7.1 | 5.8 | 6.2 |
| Sodium oleate gain | 120% | 136% | 117% | 114% | 114% | 115% |

Using control DBS from the Center of Disease Control (CDC) where High Controls were made using pooled cord blood samples from presumed healthy neonates, Medium Controls were made by diluting the cord blood with red blood cell concentrate so that the target enzyme activity was 50% that of the High Controls, and Low Controls were further diluted to obtain a target enzyme activity of 5% that of the High Control. The addition of sodium oleate widens the gap between the Low Control DBS and the Medium Control DBS by approximately 25% for the ceramides. This better distinguishes the LSD+ (low activity) samples from healthy neonates in the 6-plex assay.

Any patents or publications mentioned in this specification are indicative of the levels of those skilled in the art to which the description pertains. These patents and publications are herein incorporated by reference to the same extent as if each individual publication was specifically and individually indicated to be completely incorporated by reference.

One skilled in the art will readily appreciate that the present processes are well-adapted to carry out the objects and obtain the ends and advantages mentioned, as well as those inherent therein. The present examples along with the methods, procedures, treatments, molecules and specific compounds described herein are presently representative of specific embodiments, are exemplary, and are not intended as limitations on the scope of the processes. It will be apparent that other embodiments exist and are encompassed within the spirit of the disclosure as defined by the scope of the claims.

The invention claimed is:

1. A process for detecting enzymatic activity in vitro, comprising:
contacting a sample containing a target enzyme with a substrate and one or more oleate salts wherein said salt is selected from the group consisting of sodium, magnesium, potassium, calcium, lithium and zinc, said step of contacting is performed under conditions wherein the target enzyme is lysosomal storage enzyme capable of acting on the substrate to produce an enzymatic product, and wherein said oleate salt allows for improved enzyme activity, detection of lower enzyme amounts, and/or greater reproducibility; and
detecting said enzymatic product, wherein said target enzyme is acid α-galactosidase A, acid β-glucocerebrosidase, galactocerebrosidase, acid α-glucosidase, acid sphingomylenase, α-L-iduronidase, or combinations thereof.

2. The process of claim 1 wherein said oleate salt comprises a monovalent salt.

3. The process of claim 1 wherein said oleate salt comprises a divalent salt.

4. The process of claim 3 wherein said divalent salt is magnesium, calcium, or zinc.

5. The process of claim 1 wherein said oleate salt is selected from the group consisting of sodium oleate, potassium oleate, magnesium oleate, calcium oleate, or lithium oleate.

6. The process of claim 1 wherein said step of detecting is by mass spectrometry.

7. The process of claim 1 further comprising contacting said sample with an internal standard.

8. The process of claim 7 wherein said internal standard comprises deuterium.

9. The process of claim 1 further comprising diagnosing a subject with a lysosomal storage disorder.

10. The process of claim 1, wherein the process excludes the addition of oleic acid.

11. A process for detecting enzymatic activity in vitro, comprising:
preparing a substrate component comprising combining a substrate and an oleate salt wherein said salt is selected from the group consisting of sodium, magnesium, potassium, calcium, lithium and zinc;
drying said substrate component;
contacting a sample containing a target enzyme with said substrate component in an aqueous buffer, said step of contacting is performed under conditions wherein the target enzyme is lysosomal storage enzyme capable of acting on the substrate to produce an enzymatic product; and wherein said oleate salt allows for improved enzyme activity, detection of lower enzyme amounts, and/or greater reproducibility; and detecting said enzymatic product, wherein said target enzyme is acid α-galactosidase A, acid β-glucocerebrosidase, galactocerebrosidase, acid α-glucosidase, acid sphingomylenase, α-L-iduronidase, or combinations thereof.

12. The process of claim 11 wherein said oleate salt is selected from the group consisting of sodium oleate, potassium oleate, magnesium oleate, calcium oleate, or lithium oleate.

13. The process of claim 11 wherein said aqueous buffer comprises succinic acid.

14. The process of claim 11 wherein said aqueous buffer has a pH of 4.3 to 4.0.

15. The process of claim 11 wherein said step of contacting further comprises adding an internal standard to said substrate and said oleate salt prior to drying.

16. The process of claim 11 further comprising combining said substrate component and said aqueous buffer prior to said step of contacting.

17. The process of claim 11 wherein said step of detecting is by mass spectrometry.

18. The process of claim 11 further comprising diagnosing a subject from which said sample is derived with the presence or absence of a lysosomal storage disorder.

19. The process of claim 11, wherein the process excludes the addition of oleic acid.

* * * * *